(12) United States Patent
Si et al.

(10) Patent No.: US 11,067,553 B2
(45) Date of Patent: *Jul. 20, 2021

(54) METHOD FOR DETERMINATION AND ISOLATION OF ABNORMAL SUB-SENSORS IN A MULTI-CORE SENSOR

(71) Applicant: NOVA FITNESS CO., LTD., Shandong (CN)

(72) Inventors: Shuchun Si, Jinan (CN); Lining Liu, Jinan (CN); Jiangshan Song, Jinan (CN); Jian Gao, Beijing (CN); Michael Jun Xu, Lyons (FR)

(73) Assignee: NOVA FITNESS CO., LTD., Jinan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/984,044

(22) Filed: Aug. 3, 2020

(65) Prior Publication Data

US 2020/0363386 A1 Nov. 19, 2020

Related U.S. Application Data

(63) Continuation of application No. PCT/IB2018/055531, filed on Jul. 25, 2018.

(30) Foreign Application Priority Data

Feb. 1, 2018 (CN) .......................... 201810102149.9

(51) Int. Cl.
*G01N 33/00* (2006.01)
*G01N 15/06* (2006.01)
(Continued)

(52) U.S. Cl.
CPC ......... *G01N 33/0006* (2013.01); *G01D 21/02* (2013.01); *G01N 15/0205* (2013.01);
(Continued)

(58) Field of Classification Search
CPC ................... G01D 21/02; G01N 15/06; G01N 2015/0046; G01N 2015/0693;
(Continued)

(56) References Cited

U.S. PATENT DOCUMENTS 6,804,600 B1 * 10/2004 Uluyol ..................... G05B 9/02
123/479
9,396,637 B2 7/2016 Chandler et al.
(Continued)

FOREIGN PATENT DOCUMENTS

| CN | 101763053 A | 6/2010 |
|---|---|---|
| CN | 102480783 A | 5/2012 |
| CN | 105823856 A | 8/2016 |
| CN | 106958917 A | 7/2017 |

*Primary Examiner* — Nimeshkumar D Patel
*Assistant Examiner* — Gedeon M Kidanu

(57) ABSTRACT

A method for determination and isolation for abnormal sub-sensors in a multi-core sensor. It can be intelligently determined whether the reason for an abrupt dramatic change in sensor data is a sensor fault or sudden pollution, so as to increase data reliability. A data online rate is increased if a repair can be performed via automatic determination when a device fault occurs, which has significant value for continuous monitoring required for a haze treatment operation. In addition, human and material resources for device maintenance may be saved, thereby reducing waste.

20 Claims, 12 Drawing Sheets

(51) Int. Cl.
*G08C 17/02* (2006.01)
*G01D 21/02* (2006.01)
*G01N 15/02* (2006.01)
*G01N 15/12* (2006.01)
*G01N 15/10* (2006.01)
*G01N 15/00* (2006.01)

(52) U.S. Cl.
CPC ......... *G01N 15/0211* (2013.01); *G01N 15/06* (2013.01); *G01N 15/1012* (2013.01); *G01N 15/12* (2013.01); *G01N 33/007* (2013.01); *G01N 33/0032* (2013.01); *G08C 17/02* (2013.01); *G01N 2015/0046* (2013.01); *G01N 2015/0693* (2013.01)

(58) Field of Classification Search
CPC ........... G01N 33/0006; G01N 33/0032; G01N 33/007; G08C 17/02; H04Q 2209/50; H04Q 9/00
USPC ....................... 73/1.06, 12.09, 1.35, 862.333
See application file for complete search history.

(56) References Cited

U.S. PATENT DOCUMENTS

2010/0274444 A1* 10/2010 Williamson ........... B64D 39/00
701/29.8
2020/0363385 A1* 11/2020 Xu ..................... G01N 33/0032

* cited by examiner 100 101 102 104

METHOD FOR DETERMINATION AND ISOLATION OF ABNORMAL SUB-SENSORS IN A MULTI-CORE SENSOR

CROSS-REFERENCE TO RELATED APPLICATIONS

This application is a continuation of International Application No. PCT/IB2018/055531, filed on Jul. 25, 2018, and Chinese Patent Application No. 201810102149.9, filed on Feb. 1, 2018. The content of the aforementioned applications, including any intervening amendments thereto, is incorporated herein by reference.

TECHNICAL FIELD

This application relates to environmental monitoring, and particularly to a method for determination and isolation of abnormal sub-sensors in a multi-core sensor.

BACKGROUND OF THE DISCLOSURE

The monitoring indicators of atmospheric pollutants in environmental monitoring include sulfur dioxide, nitrogen oxides, ozone, carbon monoxide, $PM_1$ (particles with aerodynamic particle size less than 1 μm), $PM_{2.5}$ (particles with aerodynamic particle size less than 2.5 μm), $PM_{10}$ (particles with aerodynamic particle size less than 10 μm), $PM_{100}$ (particles with aerodynamic particle size less than 100 μm), and VOCs (volatile organic compounds) or TVOC (total volatile organic compounds). The atmospheric environment monitoring system can collect and process the monitoring data, and reflect the air quality condition and change law of the regional environment in a timely and accurate manner.

At present, the atmospheric environment monitoring equipment mainly includes fixed monitoring stations and mobile monitoring equipment. The current fixed monitoring stations are mainly divided into large fixed monitoring stations and small stations. Mobile monitoring equipment mainly includes special atmospheric environmental monitoring vehicles, drones and handheld devices. The aforementioned small monitoring stations and handheld devices all use air quality sensors to measure pollutants in the atmosphere. Small sensors have the characteristics of low cost, miniaturization and online monitoring, and can be used on a large scale. However, the air quality sensor itself has errors due to various reasons that cause the measured value to be inconsistent with the true value, and it also has lower accuracy, poor stability, large errors, and requires frequent calibration compared with large precision instruments or manual monitoring methods.

The laser scattering method for air pollution particulate matter sensors has a broad market prospect because of its low cost and portability. However, the portable analysis device using the scattering method has disadvantages such as poor measurement consistency, large noise, and low measurement accuracy. The core device is susceptible to various environmental factors, and fluctuations easily cause misjudgment.

When the sensor data changes suddenly and sharply, being able to intelligently determine whether the change is due to sensor failure or sudden pollution will greatly improve the reliability of the data and is of great value for ensuring the quality of monitoring data. When the equipment fails, if it can be repaired automatically, the online rate of the data can also be greatly improved, which is of great value for the continuous monitoring required for haze control. At the same time, it can save manpower and material resources in equipment maintenance and reduce social waste.

Chinese Patent Application Publication No. 105823856 A discloses an air quality monitoring method based on multi-sensor fusion, which fuses multiple sets of measurement data from multiple sensors to optimize the problem of pseudo-random errors introduced by the fluctuation of light. The data fusion method can select the existing fusion algorithm according to the requirements.

The article discloses that when the scattering method is used to measure pollutants in the air, the emitted laser is in the range of several hundred nanometers to more than one thousand nanometers, and for $PM_{2.5}$ (particle diameter below 2500 nm) and $PM_{10}$ (particle diameter below 10000 nm) pollutants to be tested, the visible laser wavelength is equivalent to the particle size of the pollutant to be measured. The laser light shows both fluctuation and particle at the same wavelength, and the scattering effect used by the light scattering method can only be measured by the particle of light, so the one time measurement cannot fully accurately represent the number of particles in the space to be measured.

SUMMARY OF THE DISCLOSURE

Terminology

Sensor: A sensor is a detection device that can sense the concentration information of pollutants and can convert the sensed information into electrical signals or other required forms of information output in accordance with a certain rule to meet the transmission, processing, storage, display, record, and control requirements. The pollutants in this article mainly include particulate matter ($PM_1$, $PM_{2.5}$, $PM_{10}$, $PM_{100}$), nitrogen oxides, sulfur dioxide, ozone, VOCs/TVOC and carbon monoxide.

Sub-sensor: It is also called sensor unit. In this article, the sensor unit includes fan, sensing element, MCU, signal conversion element and signal amplification circuit. It can independently complete the collection and calculation of pollutant data and can also transmit local storage data.

Sensor module: The sensor module is a sensor device composed of multiple sub-sensors. The sub-sensors are also called cores in the sensor module. For example, a sensor module composed of four sub-sensors is called a quad-core sensor, and a sensor module composed of five sub-sensors is also called a five-core sensor.

Abnormal fluctuation of sub-sensor: indicates that the discrete degree of the measurement results of the sensor during continuous measurement exceeds the normal range.

Abnormal drift of sub-sensor: It means that the average value of the measurement result of the sensor during continuous measurement is shifted from the true value beyond the normal range.

Abnormal correlation of sub-sensor: indicates that the correlation between the measurement result and other sensors during the continuous measurement is lower than the normal range.

Abnormal of sub-sensor: Abnormal fluctuation of sub-sensor, abnormal drift of sub-sensor, and abnormal correlation of sub-sensor are all abnormal of sub-sensor.

Abnormal sub-sensor: Also called a fault sub-sensor, it is a sub-sensor in which the abnormal phenomenon of the sub-sensor occurs.

The suspected abnormal sub-sensor: Also called suspected faulty sub-sensor, in the sensor module, the sub-sensor with the largest fluctuation or drift does not trigger the isolation condition. The suspected abnormal sub-sensor is the closest abnormal of sub-sensor among the normal sub-sensors. For example, if the measured value deviates from the normal value by 20%, it is judged to be abnormal. Assuming that the number 1, 2 and 3 sub-sensors deviate from the normal values by 5% and 6%, 16%, then we judge the sub-sensor 3 is a suspected abnormal sub-sensor.

Isolation: The case where the sub-sensor does not participate in the operation of the value uploaded by the control module is called sub-sensor isolation.

Isolation condition: The isolation condition is used to determine whether the suspected abnormal sub-sensor needs to be isolated. Such as the value of the degree of dispersion in the abnormal fluctuation of sub-sensor, and the offset value of the abnormal drift of sub-sensor.

Recovery condition: The recovery condition is the basis for judging whether the sub-sensors in the isolation zone will resume work. The standard of the recovery condition should be appropriately higher than the isolation condition.

Rotational rest method: It is a kind of working method of sub-sensors, which means that the sub-sensors start and stop work alternately at intervals.

Data deterioration: indicates that the range of sensor value deviates from the normal value increases.

Due to various reasons, for example, the performance of the sensor itself and the influence of external interference, there is often a small error between the measured value and the true value of the air quality sensor. Reducing errors and improving accuracy are the efforts in the field of sensors.

There are also many ways to improve sensor accuracy.

The first method is to use a single high-cost and high-precision sensor, but the problems brought by it are also obvious. In addition to the high cost problem, it is not possible to determine whether the sensor is abnormal through the data output by the sensor itself.

The second method is a dual-core sensor, which independently measures and outputs the results through two sensors. This method can compare the output results of the two sub-sensors according to a certain judgment standard to determine whether the sub-sensor works abnormally, but this method cannot determine which sub-sensor has an abnormality.

The third method is a triple-core sensor. By comparing the output results of the three sub-sensors, it is determined which sub-sensor has a problem, and then isolate the sub-sensor. However, since the sensor module runs in dual-core mode after isolating a sub-sensor, there will be a problem that the abnormal sensor cannot be judged. Therefore, once one sub-sensor of the three-core sensor is abnormal, the reliability of the whole sensor module is greatly reduced.

FIG. 1 shows the working state of the sub-sensor. The sub-sensor 100 indicates a normal sub-sensor. The sub-sensor 101 and the sub-sensor 102 are suspected abnormal sub-sensors. The sub-sensor 104 indicates an abnormal sub-sensor. In FIG. 2, 1U indicates a one-core sensor mode. When the sensor data is abnormal, it cannot be determined whether the sensor itself is faulty or the air quality is abnormal. 2U indicates a dual-core sensor module. When the dual-core sensor module has a sub-sensor output abnormal, it cannot determine which one is abnormal, so one sub-sensor of the dual-core sensor module is abnormal, and the entire module cannot work normally. By analogy, 3U represents a three-core sensor module.

In view of the above-mentioned shortcomings, the present disclosure provides a multi-core sensor and a method for isolating and recovering. The disclosure uses at least four sensor units to form a sensor module, which realizes complementary data deviations and mutual verification, and improves the reliability, consistency, accuracy and life of the sensor module.

As shown in FIGS. 3 and 4, 4U represents a quad-core sensor module. When a sub-sensor is found to have a suspected abnormality and it is determined that the suspected abnormal sub-sensor is an abnormal sub-sensor, it can be isolated. The quad-core sensor module downgraded to a three-core sensor module, the three-core sensor module can still work normally. 5U means a five-core sensor module. When a sub-sensor is found to have a suspected abnormality, and the suspected abnormal sub-sensor is an abnormal sub-sensor, the five-core sensor module is downgraded to a quad-core sensor module, and the quad-core sensor module can still work normally; and so on, the six-core sensor module, the seven-core sensor module and more core sensor modules.

The multi-core sensor includes a gas separation box, a control module and a detection module. The gas separation box is used to distribute the measured gas to each individual sub-sensor. The gas inlet of the gas separation box is connected to the gas sampling head, and the gas outlet is connected to the air inlet of each sub-sensor of the detection module. The detection module is a sensor module with four or more sub-sensors built in and it is used to detect the concentration of atmospheric pollutants. The control module is used to receive, analyze and upload the data detected by the detection module, and supply power to the detection module.

The sub-sensor types include $PM_1$ sensor, $PM_{2.5}$ sensor, $PM_{10}$ sensor, $PM_{100}$ sensor, sulfur dioxide sensor, nitrogen oxide sensor, ozone sensor, carbon monoxide sensor, VOCs sensor, TVOC sensor and other sensors that can measure the concentration of environmental pollutants.

Sensor accuracy is related to many factors, such as the measured gas flow rate and temperature. The disclosure further improves the accuracy of the sensor module by designing in various ways.

Sensor accuracy is related to temperature. As shown in FIG. 8, the sensor has an optimal operating temperature range. When the temperature is higher than the optimal operating temperature, the accuracy will decrease. In the disclosure, the temperature of the sensor and the intake air are adjusted by a temperature control device, and can be compensated by an algorithm to improve the detection accuracy.

The accuracy of the sensor is also related to the flow rate of the measured gas flowing inside the sensor. As shown in FIG. 9, the measured gas has the highest accuracy at the optimal flow rate $V_0$. Too fast or too slow the measured gas flow rate will affect the accuracy. The internal air resistance of the sensor or other reasons will cause the measured gas flow rate to change, as shown in FIG. 10. The present disclosure controls the measured gas flow rate within the optimal flow rate range by adjusting the internal fan speed or other flow rate adjustment methods to improve the accuracy.

Multi-core sensors use embedded algorithms to solve the problem of out-of-synchronization of multiple sub-sensors in detecting sampling gas due to different lengths of intake pipes, thereby obtaining more accurate detection data.

Multi-core sensors use multiple sensors to measure air quality at the same time, and the output value is the average value of multiple sensors, with high data accuracy. FIG. 5 shows the output data of the quad-core sensor module, where U1, U2, U3, and U4 are the output data of the four sub-sensors, and the solid line Average is the average of the four sensors, so the output data is smoother, stability and higher accuracy.

The disclosure also discloses a method for identifying the working state of the sub-sensor and isolation and recovery the sub-sensor. The method is shown in FIG. 11. The sensor module obtains a set of detection data at a time, and the control module filters out suspected abnormal data from this set of data, and then determines whether the corresponding sub-sensor meets the isolation condition. The sub-sensor was judged to be abnormal sub-sensor and then classified into the isolation zone; after judging that the suspected abnormal sub-sensor does not meet the isolation condition, the sub-sensor continues to work normally. The sub-sensors entering the isolation zone can stop working or continue to sample and detect, but the data output by the sub-sensors does not participate in the calculation of the output data of the main control module. Determine whether the sub-sensor entering the isolation area can self-heal. If it can self-heal, the frequency reduction will be performed. For sub-sensors that cannot self-heal, notify the operator to repair or replace them. For the sub-sensor after frequency reduction, whether it meets the recovery condition is judged. The sub-sensor that meets the recovery condition is removed from the isolation zone and resumed work. The output data is involved in the calculation of sensor module data or master control data. For the abnormal sub-sensor that does not meet the recovery condition, whether it can be self-healing is determined again.

After isolating the abnormal sub-sensors in the sensor module, the average value of the remaining sub-sensor output data is used as the output result of the sensor module, and the sensor module can continue to be used normally. The sensor module has normal lifetime, high precision and high online rate of equipment and high data consistency.

The present disclosure sets a rotational rest mode for the sensor module. Among the sub-sensors that work normally, one or more sub-sensors are selected for the rotational rest, which can ensure the detection accuracy while extending the life of the sensor module.

The disclosure has low use cost. Compared with expensive precision instruments, the sensor module only adds a few sub-sensors, which does not significantly increase the overall cost of the device. However, Due to the increase in reliability and accuracy, it is also possible to apply low-precision, low-reliability but low-cost sensors to situations where only high-precision instruments can be used. The multi-core sensor module also extends the life and maintenance cycle of the entire monitoring equipment, reducing the cost of equipment replacement and repair.

Sensor failure judgment can be done through the local master control, or through the data center online monitoring system. The online monitoring system is responsible for receiving data, storing, data processing, and generating visual pollution cloud maps.

Figure 1:
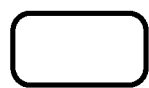
FIG. 1 is the schematic diagram of a state of a sub-sensor.
Figure 1:
Figure 1:
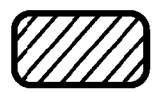
Figure 1:
Figure 2:
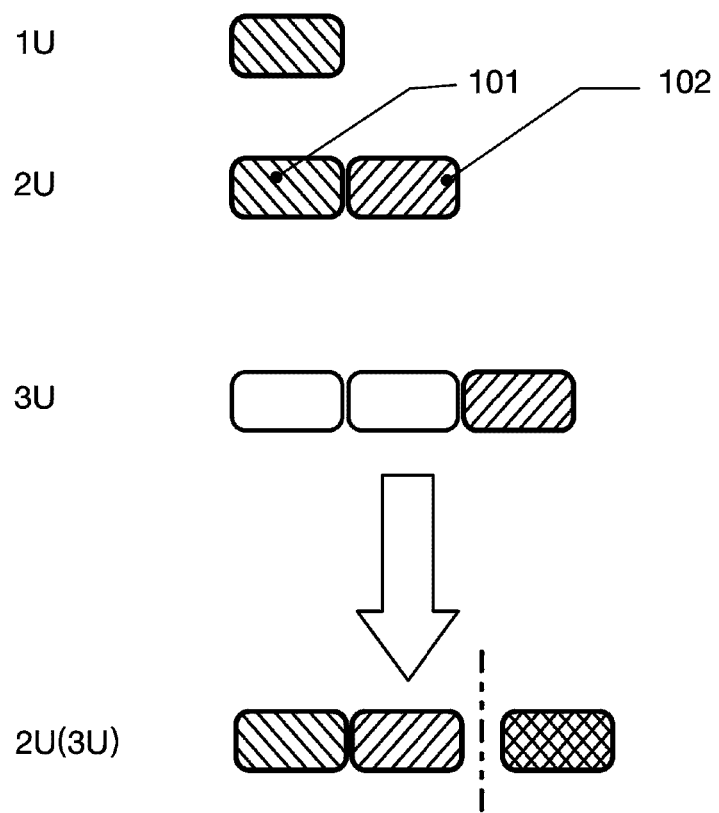
FIG. 2 is the schematic diagram of a single sensor failure of a single-core sensor module, a dual-core sensor module, a triple-core sensor module, and a triple-core sensor module.

In the drawings: 100—normal sensor, 101—suspected abnormal sub-sensor (one), 102—suspected abnormal sub-sensor (two), 104—abnormal sub-sensor, U3—sensor 3, U3—d-status indicator (Red-fault), U4—d-status indicator (green-normal); 2U (3U)—represents a group of three-core sensors operating in two-core mode, with one core isolated.

DETAILED DESCRIPTION OF EMBODIMENTS

The multi-core sensor includes a gas separation box, a control module and a detection module. The gas separation box is used to distribute the measured gas to each individual sub-sensor. The gas inlet of the gas separation box is connected to the gas sampling head, and the gas outlet is connected to the air inlet of each sub-sensor of the detection module. The detection module is a sensor module with four or more sub-sensors built in and it is used to detect the concentration of atmospheric pollutants. The control module is used to receive, analyze and upload the data detected by the detection module, and supply power to the detection module. The gas separation box has a buffer function to relieve pressure fluctuations.

The control module is provided with a control module data communication interface that it and the sensor data communication interface are connected by wires. The sensor transmits data to the control module through the data communication interface of the control module connected to the sensor. The detection module is connected to the control module through a data interface. The control module can not only process the detection data of the sub-sensors, but also upload the data to the data center through the wireless network to implement the data uploading and positioning functions. The data center is responsible for receiving data, storing and processing data. The online monitoring system can manually control the secondary calibration of the abnormal sensor.

Figure 3:
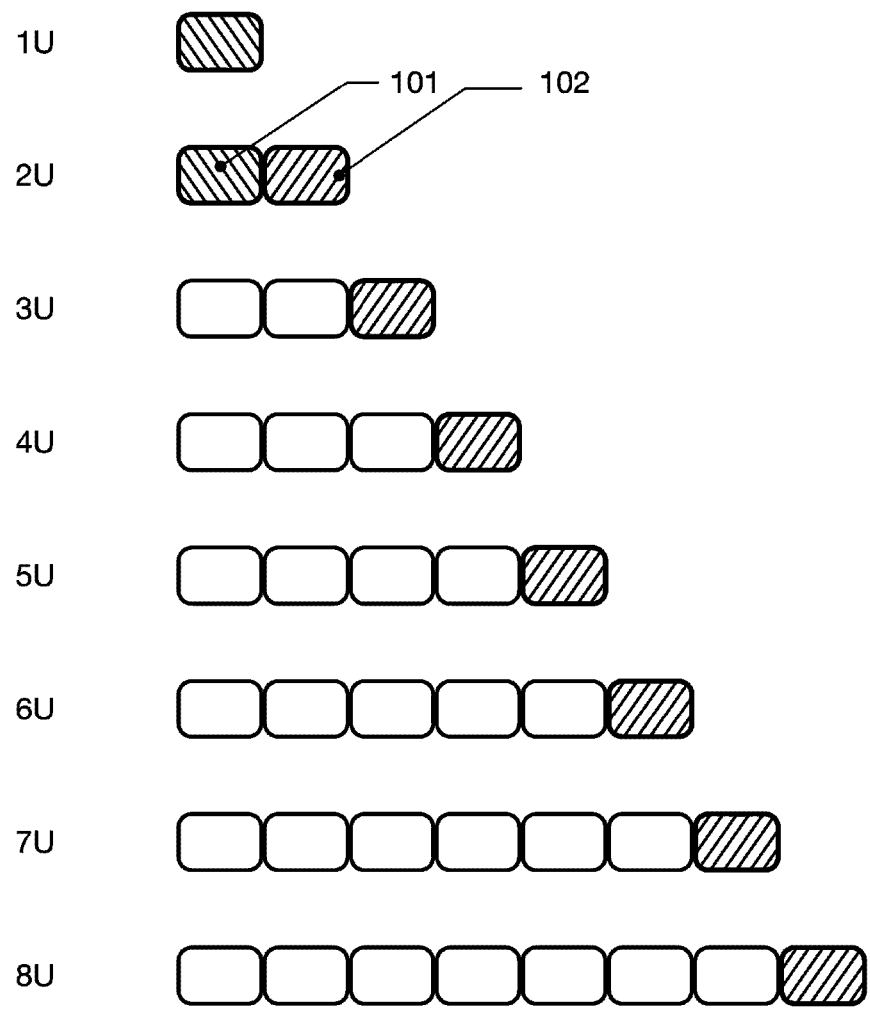
FIG. 3 is the schematic diagram of judging a suspected abnormal sub-sensor module. For one-core and dual-core sensor modules, abnormal conditions cannot be determined after suspected abnormalities; sensor modules with three or more cores can determine sensors suspected of abnormalities.
Figure 4:
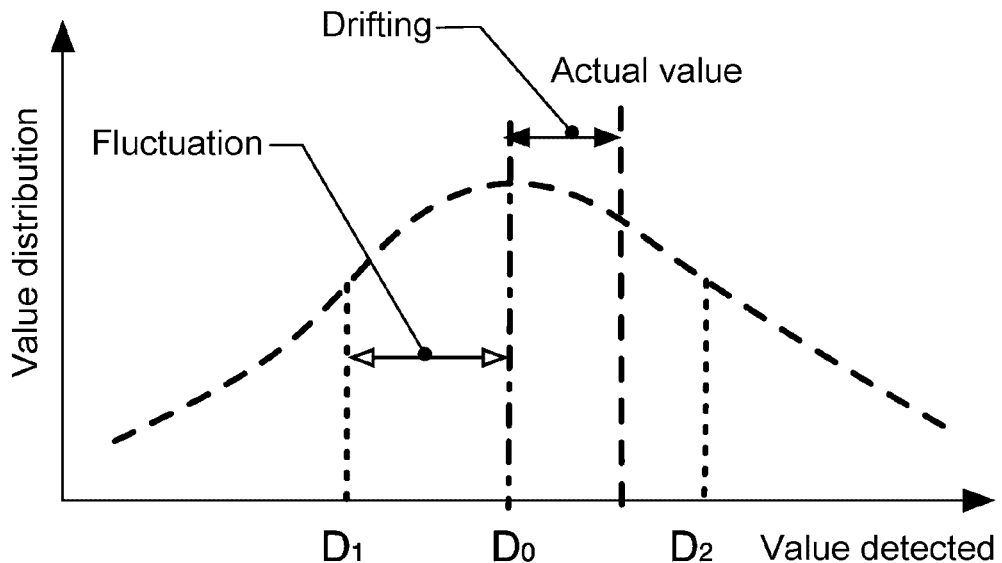
FIG. 4 is the sensor error diagram, $D_0$ and $D_1$ are fluctuations; $D_0$ and actual values are drifting.
Figure 5:
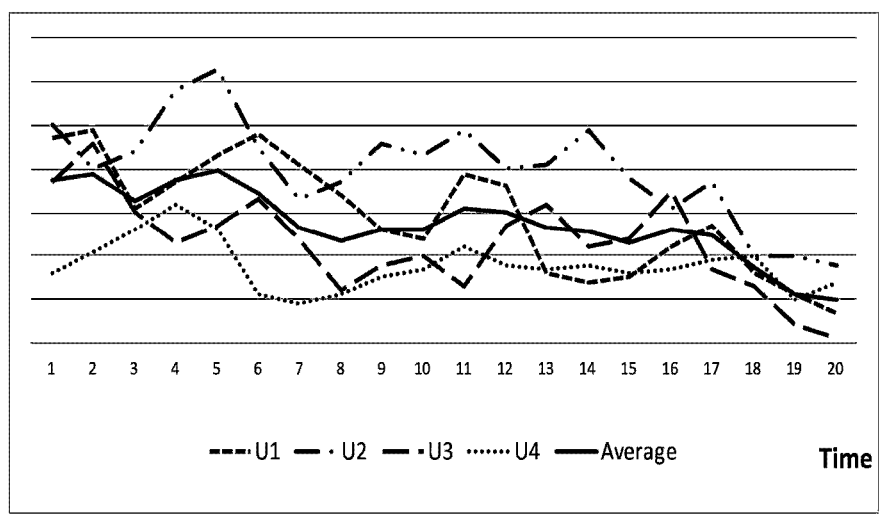
FIG. 5 is a schematic diagram of the output data of the quad-core sensor module and its sub-sensor output, Average is the quad-core average output result, and the dotted line is the output result of each core.
Figure 6:
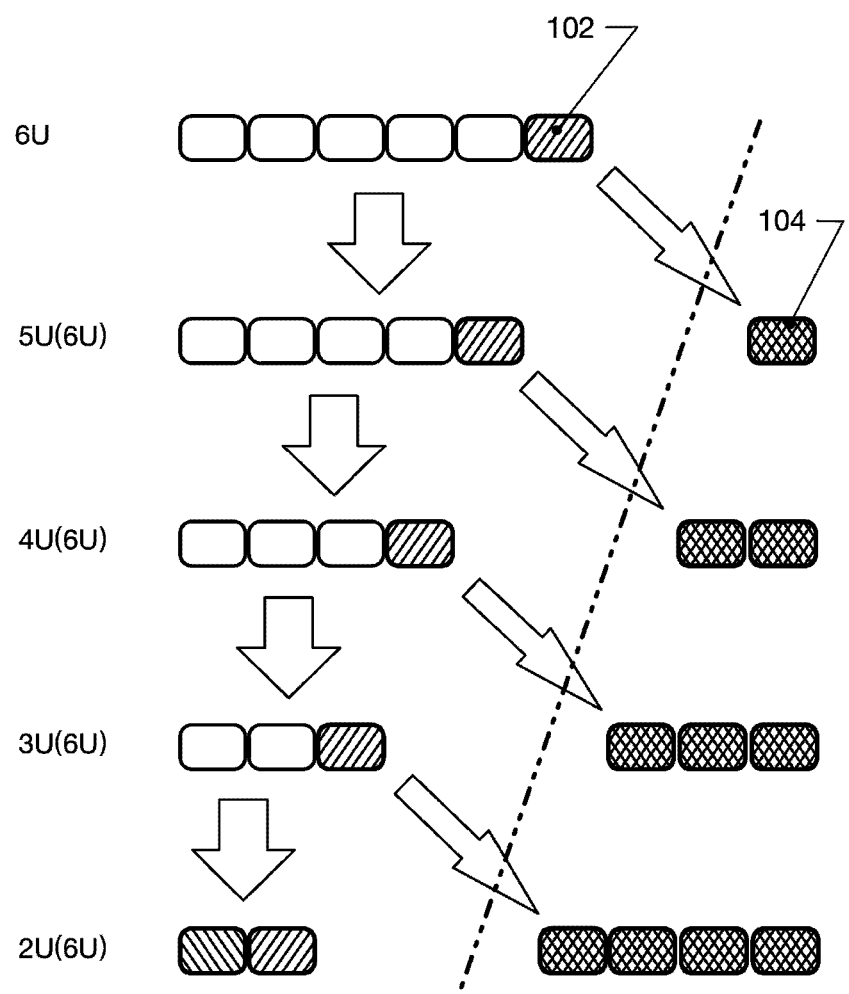
FIG. 6 is the schematic diagram of an isolation method for an abnormality of a sub-sensor of a six-core sensor module.
Figure 7:
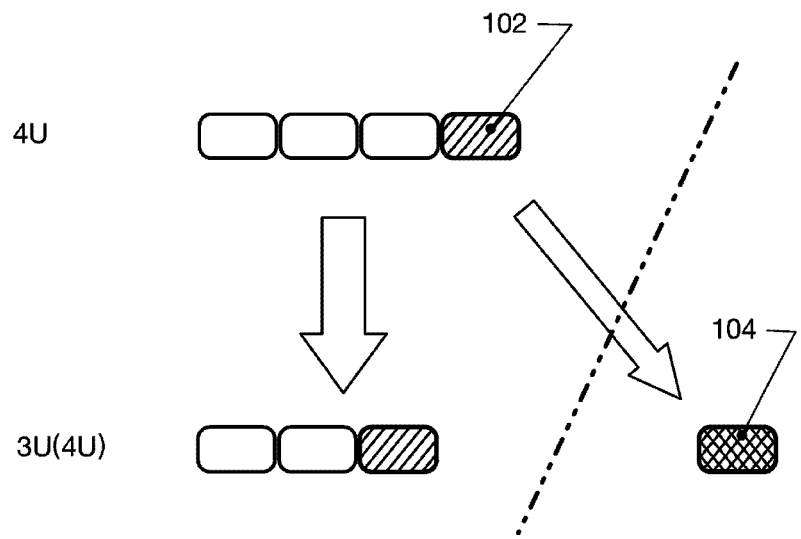
FIG. 7 is a schematic diagram of isolation and recovery an abnormal sensor in a quad-core sensor module.
Figure 7:
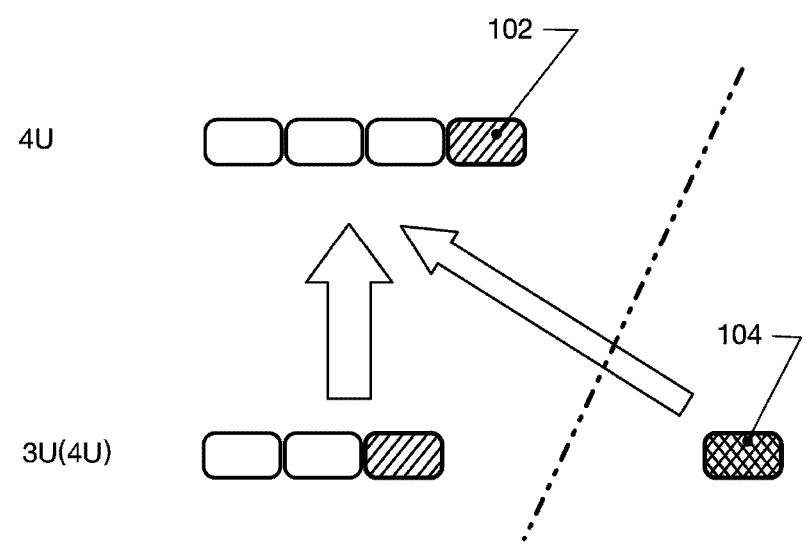

The disclosure adopts at least four sensor units to form a sensor module, which realizes complementary data deviations and mutual verification, and improves the reliability, consistency, accuracy and life of the sensor module. As shown in FIGS. 3 and 4, 4U represents a quad-core sensor module. When a sub-sensor is found to have a suspected abnormality and it is determined that the suspected abnormal sub-sensor is an abnormal sub-sensor, it can be isolated. The quad-core sensor module downgraded to a three-core sensor module, the three-core sensor module can still work normally. 5U means a five-core sensor module. When a sub-sensor is found to have a suspected abnormality, and the suspected abnormal sub-sensor is an abnormal sub-sensor, the five-core sensor module is downgraded to a quad-core sensor module, and the quad-core sensor module can still work normally; and so on, the six-core sensor module, the seven-core sensor module and more core sensor modules.

Humidity and Temperature Adjustment

Figure 8:
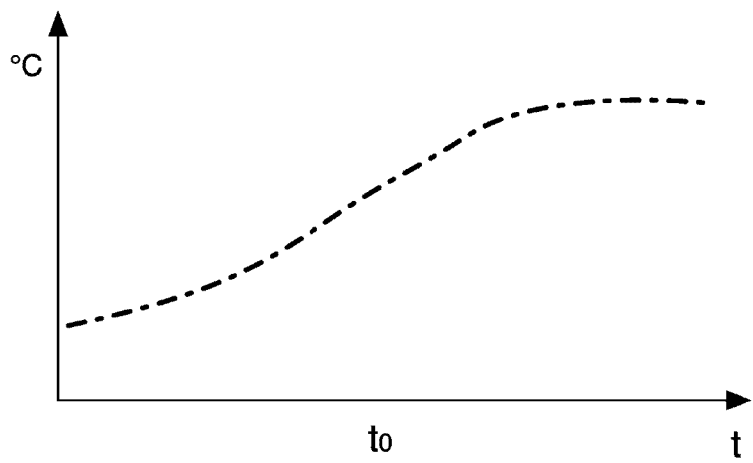
FIG. 8 is a schematic diagram of the relationship between the accuracy of the sensor and the temperature.
Figure 8:
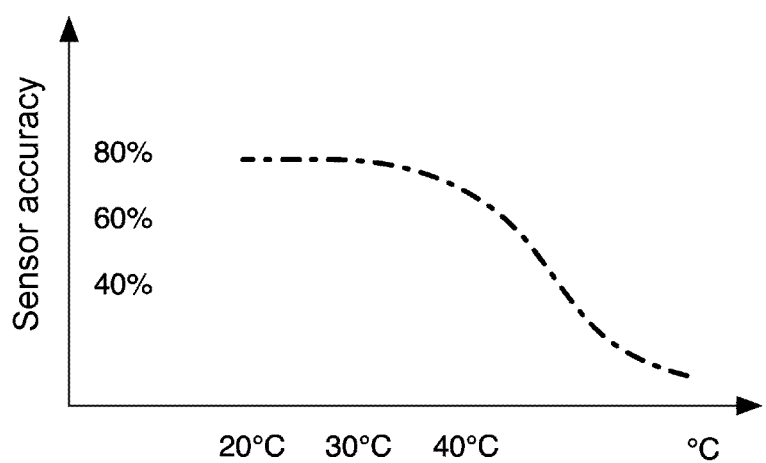

Sensor accuracy is related to temperature. As shown in FIG. 8, the sensor has an optimal operating temperature range. When the temperature is higher than the optimal operating temperature, the accuracy will decrease. In the disclosure, the temperature of the sensor and the intake air are adjusted by a temperature control device.

Embodiment One

The gas separation box can be equipped with a semiconductor refrigerating sheet made of metal and capable of heating and dehumidifying. The semiconductor refrigeration chip includes a hot end and a cold end. Use the hot end of the semiconductor refrigeration chip to directly heat the gas separation box, and install a humidity sensor before the gas inlet of the gas separation box. The system turns on the semiconductor refrigeration chip when the humidity of the gas measured is greater than the set value upper limit (the upper limit of the set value can be 60%, 65%, 70%, etc.); when the humidity is less than the lower limit of the set value (the lower limit of the set value can be 40%, 50%, etc.), the semiconductor refrigeration chip is turned off.

Embodiment Two

The gas separation box can be equipped with a semiconductor refrigerating sheet with heating and dehumidification functions, and the material is metal. The semiconductor refrigerating sheet includes a hot end and a cold end. The gas separation box is directly heated by the hot end of the semiconductor refrigerating sheet, and the cold end of the semiconductor refrigerating sheet is connected to the heat-dissipating grille, and the heat is absorbed to the air-distributing box through the heat-dissipating grille. Install a humidity sensor before the air inlet of the gas separation box. The control module turns on the semiconductor refrigerating sheet when the humidity of the gas measured is greater than the set value upper limit (the upper limit of the set value can be 60%, 65%, 70%, etc.); when the humidity is less than the lower limit of the set value (the lower limit of the set value can be 40%, 50%, etc.), the semiconductor refrigeration chip is turned off.

Embodiment Three

The gas separation box can be equipped with a semiconductor refrigerating sheet made of metal and capable of heating and dehumidifying. The semiconductor refrigeration chip includes a hot end and a cold end. Use the hot end of the semiconductor refrigeration chip to directly heat the gas separation box, the cold end of the semiconductor refrigerating chip is connected to an air pump to dissipate heat for the air pump. Install a humidity sensor before the gas inlet of the gas separation box. The system turns on the semiconductor refrigeration chip when the humidity of the gas measured is greater than the set value upper limit (the upper limit of the set value can be 60%, 65%, 70%, etc.); when the humidity is less than the lower limit of the set value (the lower limit of the set value can be 40%, 50%, etc.), the semiconductor refrigeration chip is turned off.

Compensation of Flow Rate, Temperature, Power and Pipeline Length

Figure 9:
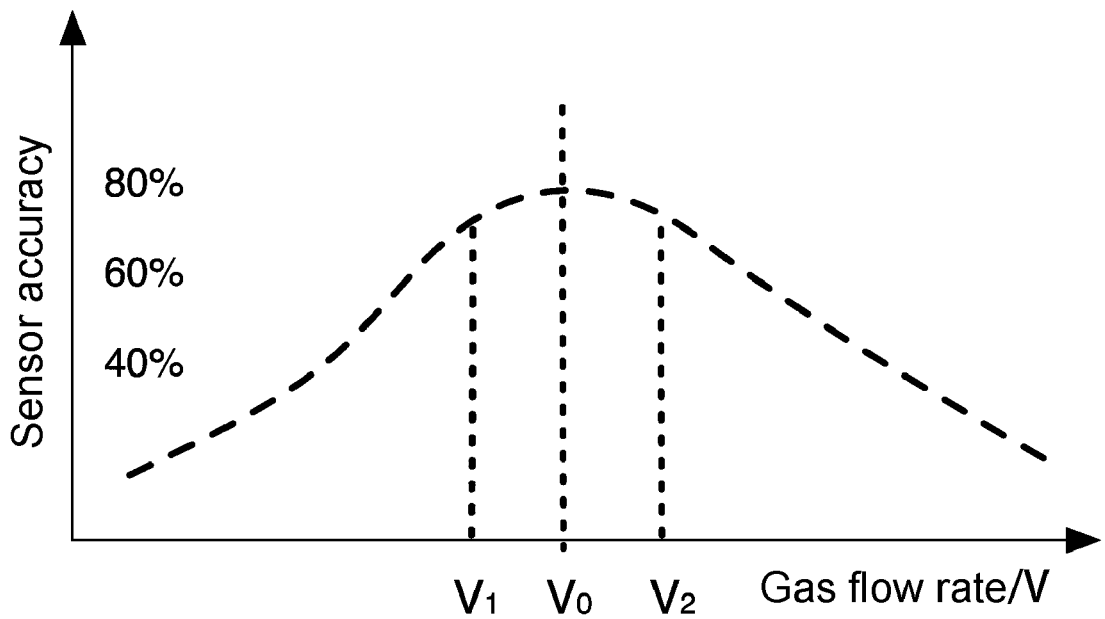
FIG. 9 shows the relationship between the sensor accuracy and the measured gas flow rate.
Figure 10:
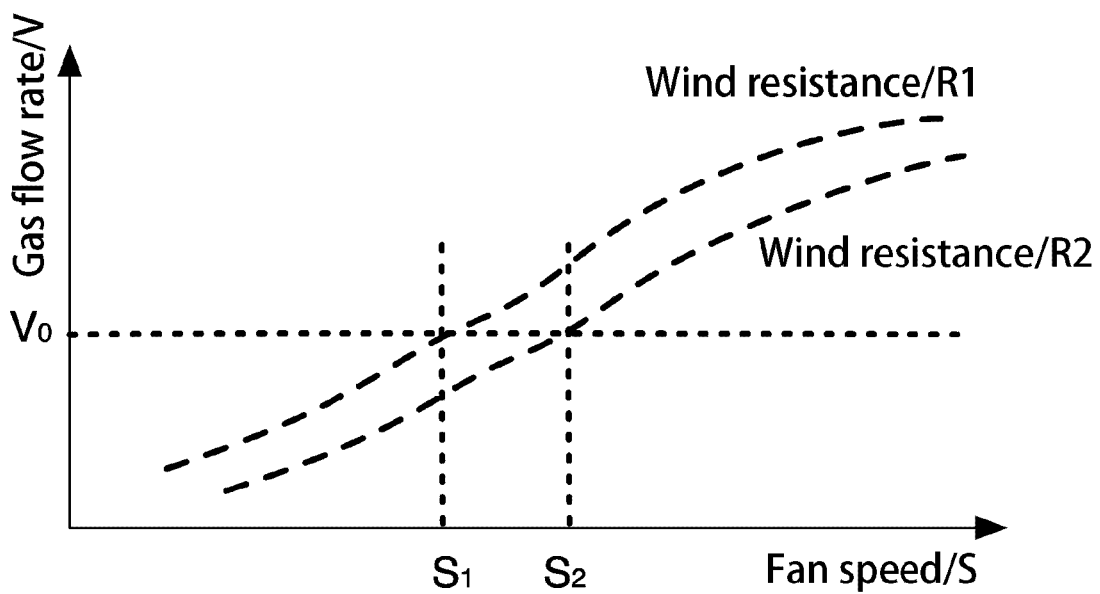
FIG. 10 is a schematic diagram showing the relationship between fan speed, wind resistance and measured gas flow rate.

The accuracy of the sensor is also related to the flow rate of the measured gas flowing inside the sensor. As shown in FIG. 9, the accuracy of the measured gas is within the range of $V_1$ to $V_2$ with the optimal flow rate $V_0$ as the center. The accuracy of the measured gas flow rate is too fast or too slow. The internal air resistance of the sensor or other reasons will cause the measured gas flow rate to change. As shown in FIG. 10, the present disclosure controls the measured gas flow rate to the optimal flow rate by adjusting the internal fan speed ($S_1$, $S_2$) or other flow rate adjustment methods. Within range, improve sensor accuracy. Multi-core sensors use embedded algorithms to compensate for the problem of asynchronous sampling of multiple sub-sensors caused by different lengths of intake pipes, thereby obtaining more accurate detection data. Similarly, temperature and humidity are compensated by corresponding algorithms to improve data accuracy.

Embodiment Four

By controlling the speed of the fan, the sampling flow is compensated. The flow rate and differential pressure sensor are used to obtain the gas flow rate, and a fan speed control circuit is added at the same time. The fan speed is controlled by the obtained gas flow rate information, so that the sampling gas flow rate is stabilized, within a range of preferred flow rate, as shown in $V_0$ of FIGS. 9 and 10. The optimal flow rate of the sensor is based on experimental methods to obtain empirical values.

Embodiment Five

For the laser particle sensor, a laser power detection device and a laser power control circuit are added to compensate the laser power. The change relationship of the particle concentration value corresponding to each laser power value is obtained experimentally (that is, other conditions are fixed and only the measured conditions are changed to obtain the measurement results). The attenuation data is compensated by the laser power control circuit according to the detection result of the power sensor.

Embodiment Six

Take temperature compensation measures for the sensor. Install a temperature acquisition probe on the sensor or the measured gas. First, by using the experimental method or the sensor temperature characteristic data, the change relationship of the pollutant concentration value corresponding to different sampling temperature values is obtained (that is, other conditions are fixed and only the measured temperature conditions are changed). Compensate the output pollutant results based on the collected temperature data during use.

Embodiment Seven

Take humidity compensation measures for the sensor. Install humidity acquisition equipment to collect the humidity data of the measured gas. First, by using the experimental method or the humidity characteristic data of the sensor, the change relationship of pollutant concentration values corresponding to different sampling humidity values is obtained (that is, other conditions are fixed and only the humidity conditions of the measured gas are changed). Compensate the output pollutant results based on the collected humidity data during use.

Output Data Calculation Method

Multi-core sensors use multiple sensors to measure air quality at the same time, and the output value is the result of comprehensive calculation of data from multiple sensors. The data is smoother, more stable, and more accurate.

The eighth embodiment to the twelfth embodiment are data calculation methods of the sensor module. The data of the outlier sensor needs to be excluded during data calculation. For the method of determining the outlier sensor, refer to the thirteenth to the seventeenth embodiments.

Embodiment Eight

Mean value method: a method for calculating the output data of a sensor module; after excluding abnormal sensor unit data, the average value of all normal sensor unit data is taken as the output result.

Embodiment Nine

Median method: a method for calculating the output data of a sensor module; after excluding abnormal sensor unit data, the values of all normal sensor units are sorted, and the middle value of the sort is used as the final result.

The number is even, then the average of the two sensor units in the middle is taken as the final result.

Embodiment Ten

Correlation coefficient method: a method for calculating the output data of a sensor module; after excluding abnormal sensor unit data, calculate the normal sensor unit data as follows to obtain the final result.

The storage unit stores the historical detection data of each sensor unit, and calculates the values of the judged sensor unit and other sensor units by using the historical data of a period (1 minute, 10 minutes, 20 minutes, . . . 1 hour) as a time unit.

Correlation coefficient, the calculation method of the above correlation coefficient:

A. Use the value of the selected historical time unit of the judged sub-sensor and the average value of other sensor units in that period to calculate the correlation coefficient.

B. Use the value of the selected historical time unit of the judged sub-sensor to calculate the correlation coefficient with each other sensor unit. After obtaining the result, calculate the average value of each correlation coefficient as the final correlation coefficient to obtain each normal sensor unit. After correlating coefficients with other sensor units, calculate the percentages of the correlation coefficients of all normal sensor units to the sum of the total correlation coefficients. Multiply the detection result of each normal sensor unit by this percentage and add up to get the final detection result.

Embodiment Eleven

Variance method: a method for calculating the output data of the sensor module; after excluding the abnormal sensor unit data, the normal sensor unit data is calculated as follows to obtain the final result.

The memory stores the historical detection data of each sensor unit, and uses the historical data of a period of time (1 minute, 10 minutes, 20 minutes, . . . 1 hour) as the time unit to calculate the variance Vi (or standard deviation), add the variance of each sensor unit and calculate the difference between the sum and the variance of each sensor unit. After obtaining the difference, calculate the percentage of the sum of the difference of each sensor unit. The detection result of the sensor unit is multiplied by the percentage and then added up to obtain the final detection result.

Embodiment Twelve

Percentage method: A method for calculating output data of a sensor module. After excluding abnormal sub sensor unit data, the normal sensor unit data is calculated as follows to obtain the final result.

The sensor stores the historical detection data of each sensor unit, and uses a period of time (10 seconds, 20 seconds, etc.) as the time unit to calculate the average value of the detection value in the nearest time unit, and uses the average value to calculate. The above calculation method:

A. Add up the average value of each sensor unit in the time unit to calculate the percentage of each sensor unit in the sum, and multiply the detection result of each normal sensor unit by the percentage to add the final result.

B. Using the calculation method described above, calculate the percentage of each sub-sensor in multiple time units closest to the current, average the percentage of each sensor unit in multiple time units, and get the average of each sensor unit in multiple time units closest to the current, the detection result of each normal sensor unit is multiplied by the percentage and then added up to obtain the final detection result.

Identify Sub-Sensor Working Status

Figure 11:
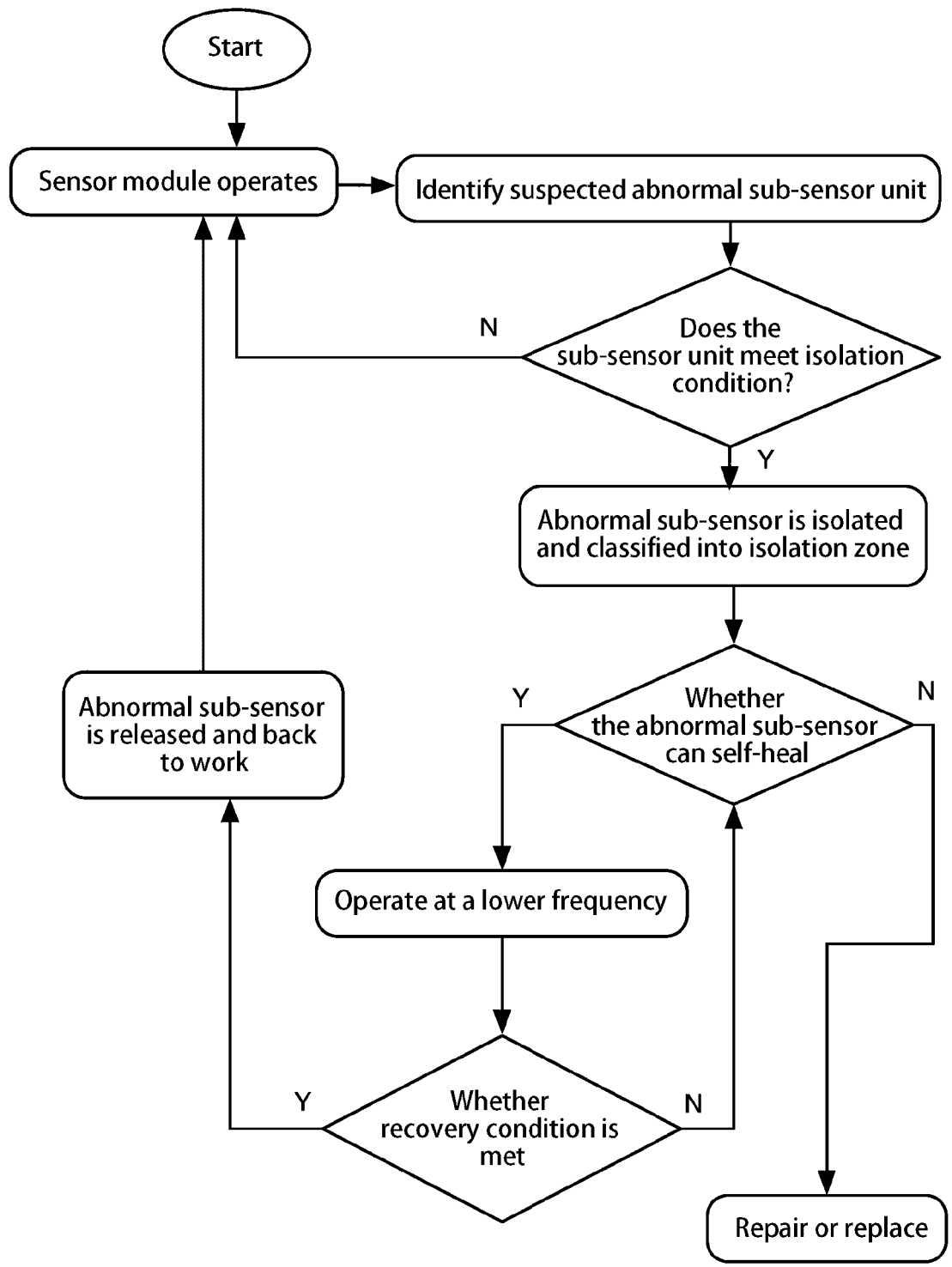
FIG. 11 is a flowchart of a method for isolation and recovery a multi-core sensor module.
Figure 12:
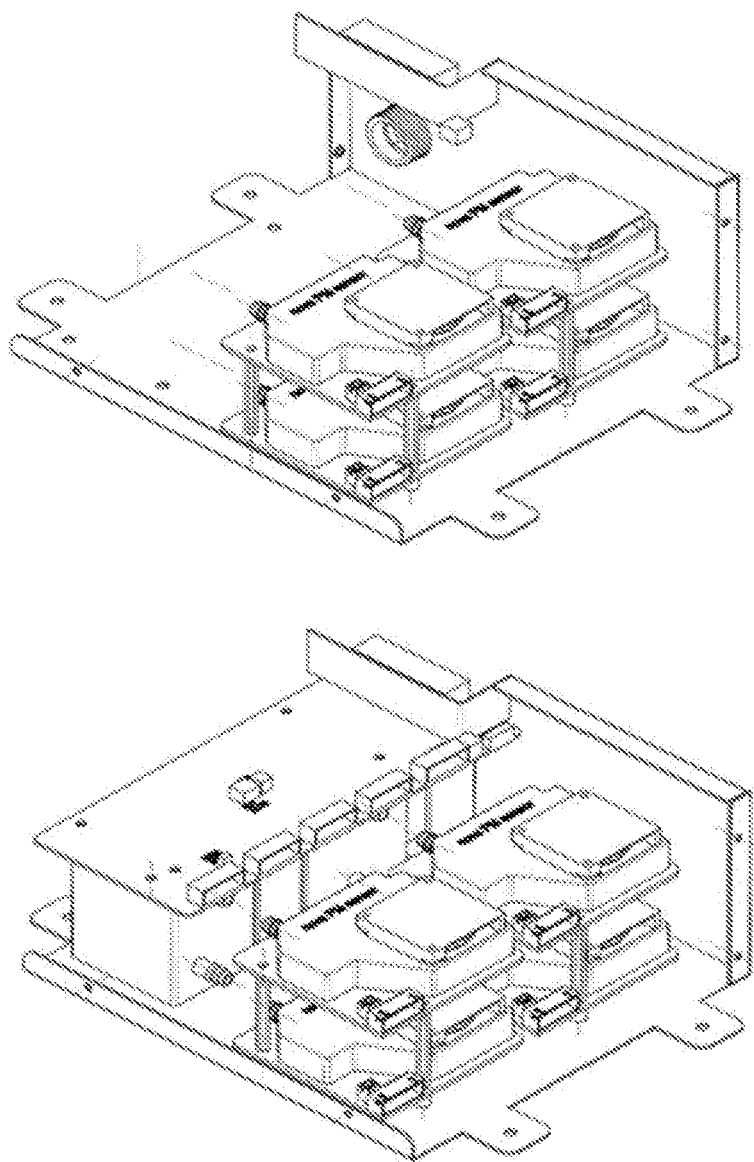
FIG. 12 is a schematic diagram of the quad-core sensor.

This solution invents set a method for identifying the working state of sub-sensors, and isolation and recovery the sub-sensors. This method is shown in FIG. 11.

1) The sensor module obtains a set of detection data at a time, and the multi-core sensor filters out suspected abnormal data from this set of data, and then determines whether the corresponding sub-sensor meets the isolation condition.

2) The sub-sensor was judged to be abnormal sub-sensor and then classified into the isolation zone; the sub-sensor continues to work after it is determining that the sub-sensor does not meet the isolation conditions. The sub-sensor entering the isolation zone can stop working or continue sampling and detection, but the data output by the sub-sensor does not participate in the calculation of the output data of the control module.

3) Determine whether the sub-sensor entering the isolation zone can heal itself: if it is judged that it can heal itself, then perform frequency reduction work on the self-healing sub-sensor, and notify the operation and maintenance party for repair or replace. For the sub-sensor after frequency reduction, determine whether it reaches the recovery condition, the sub-sensor reaching the recovery condition are detached from the isolation area and resume work, and the output data participates in the calculation of sensor module data or main control data; for abnormal sub-sensors that do not meet the recovery condition, determine whether it can heal itself.

Embodiment Thirteen

Judgment of suspected abnormal sub-sensor and abnormal sub-sensor: When the variance of the data of a certain sub-sensor exceeds the threshold, or the drift of the data of the sub-sensor exceeds the threshold, first list it as a suspected abnormal sensor instead of immediately identifying the sensor as abnormal. Finally, it is determined that the sub-sensor is abnormal only when multiple consecutive data are abnormal in a certain period of time.

Embodiment Fourteen

Comparison method of average values of sub-sensors: Take a quad-core sensor module as an example, and use the current time as a reference to compare the data of one sub-sensor with the average value of other three sub-sensors within a certain period of time (such as 5 s average, 30 s average, 60 s average, etc.)

Embodiment Fifteen

When the abnormal sub-sensor occurs, the data collected by it should be isolated and not involved in the calculation of the final output data of the sensor module. However, the abnormal sub-sensor still normally outputs data to the control module to monitor the data of the abnormal sub-sensor. Abnormal sub-sensors include abnormal drift of sub-sensor, abnormal fluctuation of sub-sensor and abnormal correlation of sub-sensor.

The storage unit stores the historical detection data of each sensor unit, and calculates respectively the value correlation coefficient of the target sensor unit and other sensor units by using the historical data of a period (1 minute, 10 minutes, 20 minutes, . . . 1 hour) as a time unit. If the correlation coefficient is less than a certain value, such as 0.5 (non-strong correlation), the correlation of the sensor is judged to be abnormal, and it does not participate in the calculation of the final result. The above correlation coefficient is calculated as follows:

A. Use the value of the selected historical time unit of the target sub-sensor and the average value of other sensor units in that period to calculate the correlation coefficient.

B. Use the value of the selected historical time unit of the sub-sensor to calculate respectively the correlation coefficient with each other sensor unit, and calculate the average value of each correlation coefficient as the final correlation coefficient after obtaining the result.

The correlation method is used to determine the abnormal correlation of sub-sensor. Taking the correlation calculation of a quad-core sensor module as an example, the correlation between the 100 sets of data of the sub-sensors and the average of the 100 sets of data of the other three sub-sensors is used for correlation calculation. If the $R^2$ is less than or equal to 0.8, the correlation between the sub-sensor data and the sub-sensor is abnormal. The sensor module selects the data of the other three sub-sensors to calculate and output the monitoring results.

Embodiment Sixteen

The sixteenth embodiment is a method for determining the abnormal fluctuation of sub-sensor. The sensor stores the historical detection data of each sensor unit, and uses the historical data of a period of time (1 minute, 10 minutes, 20 minutes, . . . 1 hour) as the time unit to calculate the variance (or standard deviation), by comparing the variance (or standard deviation) of the target sensor unit with the variance (or standard deviation) of other sensor units, the above variance comparison method:

A. Compare the variance (or standard deviation) of the target sensor unit with the mean value of the variance (or standard deviation) of other sensor units. If the difference between the two exceeds a certain value, such as 20%, 30%, etc., the abnormal fluctuation of the sensor unit will be judged.

B. Compare the variance (or standard deviation) of the target sensor unit with the variance (or standard deviation) of other sensor units respectively, and calculate the percentage of the difference between the two relative to the variance (or standard deviation) of the compared sensor unit. Select the maximum value of percentage. If it exceeds a certain value, such as 20%, 30%, etc., it is judged that the abnormal fluctuation sub-sensor.

Embodiment Seventeen

The seventeenth embodiment is a method for judging the abnormal drift of sub-sensor. The difference between the average value of the target sensor unit in the past two time units is calculated, and the percentage of the difference value and the average value in the latest time unit is calculated, and the percentage is used for judgment. The above drift judgment method:

A. Compare the percentage obtained by the target sensor unit with the average of the percentages obtained by other sensor units. If the percentage difference exceeds a certain value, such as 20%, 30%, 40%, etc., the sensor unit is judged to be drifting abnormally.

B. Compare the percentage obtained by the target sensor unit with the average of the maximum value obtained by other sensor units. If the percentage difference exceeds a certain value, such as 20%, 30%, 40%, etc., the sensor unit is judged to be drifting abnormally.

Embodiment Eighteen

In the case of the need to isolate the abnormal sensor, the data of the abnormal sensor is isolated, but the fan or air pump of the abnormal sensor continues to keep running, to ensure that the wind pressure and flow are constant, and to reduce pressure fluctuations.

Embodiment Nineteen

Figure 13:
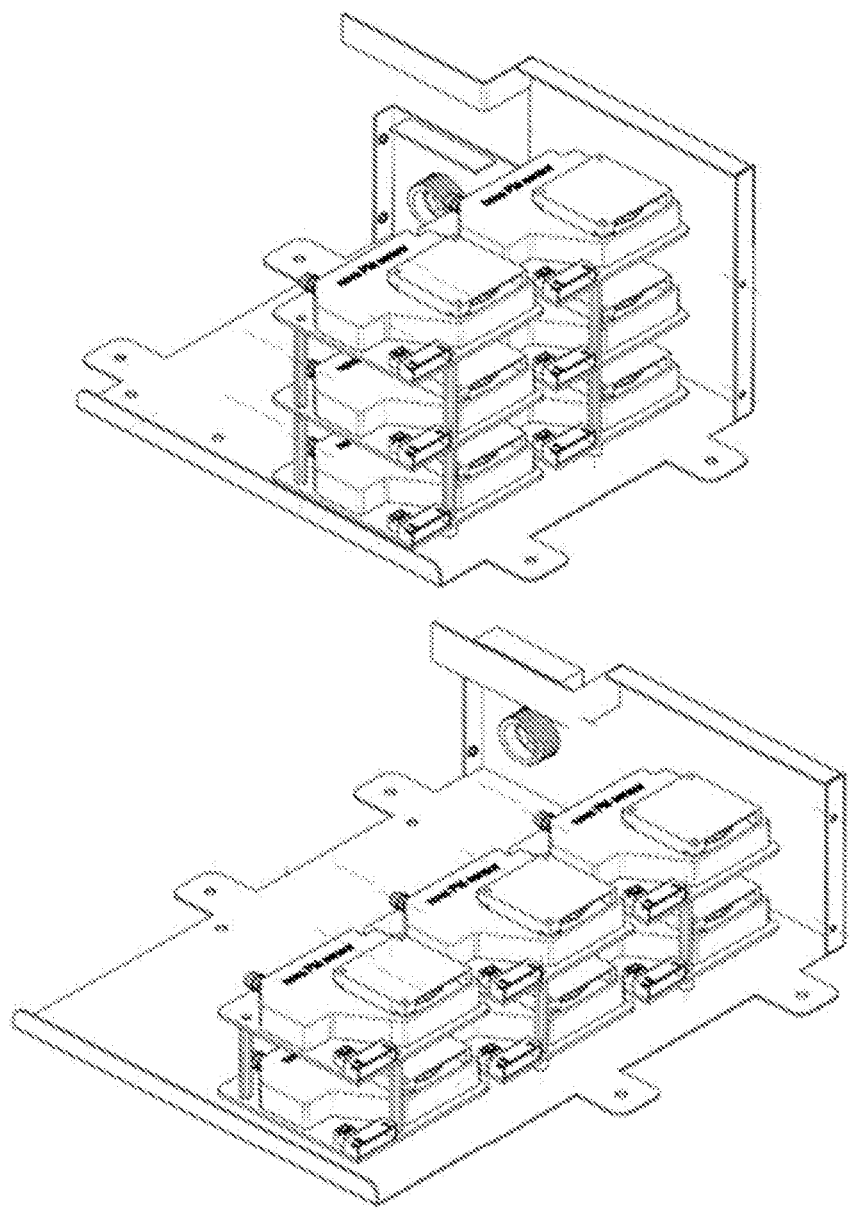
FIG. 13 is a schematic diagram of the six-core sensor and its fault indicator.
Figure 14:
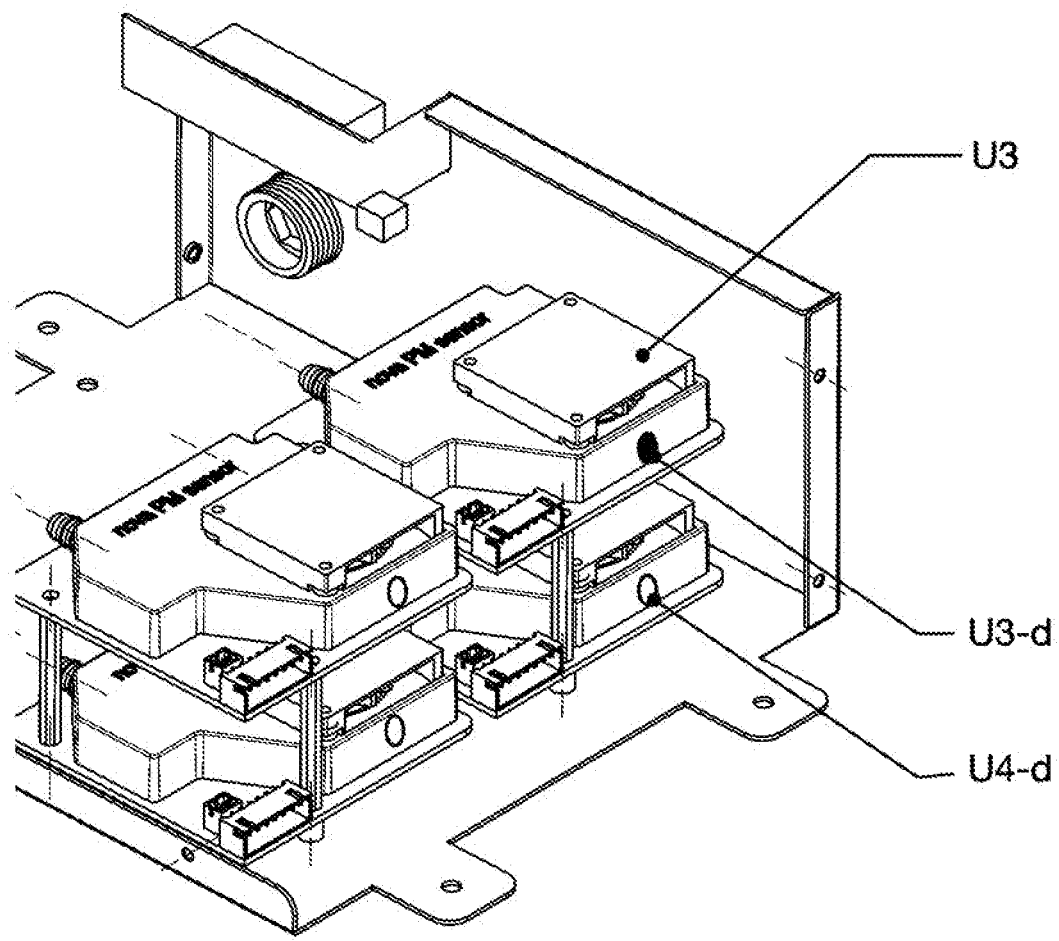
FIG. 14 is a schematic diagram of the quad-core sensor and its fault indicator.

As shown in FIG. 13, install the status indicator light on the sub-sensor. After the abnormal sub-sensor is identified, the status indicator light at the corresponding position on the communication port of the circuit board will change to a warning color (such as red). The status indicator light corresponding to the sub-sensor in normal working state is green.

Rotational Rest Mode

The disclosure sets a rotational rest working mode for the sensor module. Among the sub-sensors that work normally, one or more rotation rests are selected, that is, the fatigue problem of the sensor is solved by actively degrading the operation. The lifetime of the sensor module is extended while ensuring the detection accuracy.

Embodiment Twenty

The twentieth embodiment is a rotational rest mode of a sub-sensor. For sensor modules, rotational rest refers to turning off the sensing part of one or more sub-sensors within a specified time. For example, the laser particle sensor module using a fan only turns off the laser, and the fan does not turn off.

The off time of the sub-sensor can be a fixed time (such as 1 hour, 2 hours, 3 hours, 4 hours, 5 hours, 6 hours, 7 hours, 8 hours, 9 hours, 10 hours, 11 hours, 12 hours, 24 hours, 2 days, 3 days, 4 days, 5 days, 6 days, or 7 days, etc.), after the closed sub-sensor reaches the closing time, the closed sub-sensor is activated, and then the next sub-sensor that meets the rotational rest condition is closed. The closed time can also be determined according to the working status of other sub-sensors. For example, in a quad-core sensor module with one sub-sensor in the off state. At this time, if the system determines that one of the three sub-sensors in operation has reached the isolation condition and needs to be isolated, the sub-sensor in the closed state should be immediately enabled. The specific rotation conditions can be:

A. Select the rotational rest sensor based on the temperature change. Form 1: Select the sub-sensor with the highest temperature through the acquired sub-sensor temperature data; Form 2: Select the sub-sensor that is turned off according to the ambient temperature. If the ambient temperature is higher than the temperature set value (such as 40 degrees Celsius), it will be numbered turn off sub-sensors in turn;

B. Select the rotational rest sensor by detecting the change in the value. For confirmed suspected abnormal sensor shut down preferentially. The suspected sub-sensor can be turned off.

Embodiment Twenty-One

When three-core or more sub-sensors in the quad-core sensor module work normally, a single-core rotational rest scheme can be adopted, so as to extend the lifetime of the sensor. The lifetime of the sensor is greatly affected by temperature. When the temperature is higher than 60° C. or after four hours of normal operation, the adjacent single-core cycle rest is changed, and the rest is rotated in order to reduce the working time of the sub-sensor under high temperature and increase the working time limit of the quad-core sensor.

What is claimed is:

1. A method for determination and isolation of abnormal sub-sensors in a multi-core sensor, said multi-core sensor comprising a control module and a detection module; said detection module comprising a sensor module comprising at least four sub-sensors; said method comprising:
  1) determination of said abnormal sub-sensor: wherein said control module obtains a set of detection data at a time, and said control module filters out suspected abnormal data from the set of detection data, and then determines whether the sub-sensor meets a isolation condition;
  2) isolation of the abnormal sub-sensor: wherein a sub-sensor meeting the isolation condition is classified into an isolation zone; said sensor module continues to work after it is degraded; said sub-sensor entering the isolation zone can stop working or continue sampling and detection, but data output by the sub-sensor does not participate in the calculation of the output data of said control module;
  3) determining whether said sub-sensor entering the isolation zone can heal itself;
    wherein if it is judged that it can heal itself, then frequency reduction is performed on the self-healing sub-sensor; and
  4) recovery of said abnormal sub-sensor: wherein the output data of said sub-sensor entering the isolation zone is monitored to determine whether the sub-sensor has reached the recovery conditions; and said sub-sensor that have reached the recovery conditions are detached from the isolation zone and resume work.

2. The method of claim 1, wherein said abnormal sub-sensor is judged according to one of the following abnormalities:
  1) abnormal drift of sub-sensor;
  2) abnormal fluctuation of sub-sensor; and
  3) abnormal correlation of sub-sensor.

3. The method of claim 1, wherein the control module supplies power to the detection module.

4. The method of claim 1, wherein the sub-sensor is one of the following sensors: $PM_1$ sensor, $PM_{2.5}$ sensor, $PM_{10}$ sensor, $PM_{100}$ sensor, sulphur dioxide sensor, nitrogen oxide sensor, ozone sensor, carbon monoxide sensor, VOCs sensor, and TVOC sensor.

5. The method of claim 1, wherein the detection module comprises a plurality of sub-sensors of the same type; or the detection module comprises a plurality of sub-sensors of different types.

6. The method of claim 1, wherein the sub-sensor is a laser particulate matter sensor.

7. The method of claim 1, wherein a status indicator light is on the each sub-sensor; when the abnormal sub-sensor is identified, the status indicator light on the abnormal sub-sensor is changed to a warning color;
otherwise, the status indicator light in green.

8. The method of claim 1, wherein the multi-core sensor is improved by one of following methods:
  1) compensation for lengths difference: embedded algorithms are used to compensate for asynchronous sampling of the sub-sensors caused by different lengths of intake pipes;
  2) control of flow rate: a flow rate sensor and a differential pressure sensor are used to obtain gas flow rate, and a fan speed control circuit is added; by adjusting the speed of the fan by the fan speed control circuit, gas flow rate is stabilized, within a range of preferred flow rate;
  3) temperature compensation: a temperature acquisition probe is installed at the multi-core sensor or the measured gas, by using the experimental method or temperature characteristic data of the multi-core sensor to obtain the change relationship of the pollutant concentrations corresponding to different sampling temperatures; output results of the multi-core sensor are compensated according to measured gas temperature; and
  4) humidity compensation: a humidity acquisition device is installed to measure gas humidity, by using a experimental method or humidity characteristic data of the sensor to obtain a change relationship of pollutant concentrations corresponding to different sampling humidity values; output results of the multi-core sensor are compensated according to measured gas humidity.

9. The method of claim 1, wherein the multi-core sensor improves accuracy of detected data of the sensor module by compensation for laser power which comprises following steps: adding a laser power detection device and a laser power control circuit to compensate for laser power; experimentally obtaining a change relationship of a particle concentration value corresponding to each laser power value; and compensating attenuation data by the laser power control circuit according to the detection result of the laser power detection device.

10. The method of claim 1, wherein the multi-core sensor further comprises a gas separation box; the gas separation box distributes gas to each of the sub-sensors; the gas separation box comprises at least one gas inlet and a plurality of gas outlets; the gas outlets of the gas separation box and the gas inlets of the sub-sensors are connected via an intake pipe of the sub-sensor; the detection module is configured to detect a concentration of atmospheric pollutants; and the control module is configured to receive, analyze and upload data detected by the detection module.

11. The method of claim 10, wherein the gas separation box is arranged with a semiconductor refrigerating sheet with heating and dehumidification functions; the semiconductor refrigerating sheet is made of metal; the semiconductor refrigerating sheet includes a hot end and a cold end; the gas separation box is directly heated by the hot end of the semiconductor refrigerating sheet; there is a humidity sensor before the gas inlet of the gas separation box; when the humidity sensor detects a greater value in gas humidity than a set value upper limit, the control module turns on the semiconductor refrigerating sheet; otherwise, the semiconductor refrigerating sheet is turned off.

12. The method of claim 1, wherein after receiving detection data from the detection module, the control module analyses the detection data and calculates an output data, wherein data of abnormal sub-sensors are eliminated during calculation.

13. The method of claim 12, wherein a comprehensive calculation is performed by one of following methods: 1) mean value method; 2) median method; 3) correlation coefficient method; 4) variance method; 5) percentage method.

14. The method of claim 1, wherein on premise of ensuring at least three sub-sensors normally operate, one or more sub-sensors are selected for rotational rest, and said multi-core sensor continues to work after said multi-core sensor is degraded.

15. The method of claim 14, wherein when said multi-core sensor is a four-core sensor, one sub-sensor which reaches rotational rest conditions is selected for resting, and the four-core sensor is degraded to a triple-core sensor.

16. The method of claim 14, wherein when said multi-core sensor is a five-core sensor or a sensor comprising at least six sub-sensors, and two sub-sensors are selected for rotational rest, one sub-sensor which reaches the rotational conditions is selected, and then the other sub-sensor which reached the rotational conditions is selected from remaining sub-sensors.

17. The method of claim 14, wherein the closing time is determined according to a working status of other sub-sensors; when the control module determines that one of the three sub-sensors in operation has reached the isolation condition and needs to be isolated, the sub-sensor in the closed state is immediately enabled.

18. The method of claim 14, wherein the sub-sensor which reaches the rotational rest condition comprises any one of following sub-sensors:
   a) the sub-sensor with a least accumulated rotational rest;
   b) when temperature data of the sub-sensor can be obtained, the sub-sensor with a highest temperature; and
   c) a suspected abnormal sensor.

19. The method of claim 14, wherein an off time of said sub-sensor can be a fixed time; after a closed sub-sensor reaches a closing time, the closed sub-sensor is activated, and then a next sub-sensor that meets the rotational rest conditions is closed.

20. The method of claim 19, wherein the fixed time is 1 hour, 2 hours, 3 hours, 4 hours, 5 hours, 6 hours, 7 hours, 8 hours, 9 hours, 10 hours, 11 hours, 12 hours, 24 hours, 2 days, 3 days, 4 days, 5 days, 6 days, or 7 days.

* * * * *